United States Patent
Stapleton et al.

(10) Patent No.: US 6,606,990 B2
(45) Date of Patent: Aug. 19, 2003

(54) MOUTH PIECE FOR INHALATION THERAPY UNITS

(75) Inventors: Kevin Stapleton, Brookline, MA (US); Robert Waldner, Peiting (DE); Thomas Gallem, Munich (DE); Martin Knoch, Berg (DE)

(73) Assignee: Pari GmbH Spezialisten fur effektive Inhalation, Starnberg (DE)

( * ) Notice: Subject to any disclaimer, the term of this patent is extended or adjusted under 35 U.S.C. 154(b) by 0 days.

(21) Appl. No.: 09/223,452

(22) Filed: Dec. 30, 1998

(65) Prior Publication Data

US 2002/0056448 A1 May 16, 2002

(51) Int. Cl.[7] .............................................. A61M 11/00
(52) U.S. Cl. .......................... 128/200.18; 128/200.21; 128/200.14; 128/203.12; 128/207.14; 128/863
(58) Field of Search ....................... 128/200.24, 200.21, 128/200.22, 200.23, 205.24, 203.11, 203.29, 206.21, 206.12, 201.28, 200.18, 200.14, 203.12, 207.14, 863

(56) References Cited

U.S. PATENT DOCUMENTS

| | | | |
|---|---|---|---|
| 2,470,297 A | | 5/1949 | Fields |
| 3,848,583 A | | 11/1974 | Parr |
| 3,870,046 A | | 3/1975 | Elliott |
| 3,938,511 A | | 2/1976 | Roberts |
| 4,441,494 A | | 4/1984 | Montalbano |
| 4,456,016 A | | 6/1984 | Nowacki et al. |
| 4,884,564 A | | 12/1989 | Lamont |
| 5,239,990 A | * | 8/1993 | Delphia ................. 128/201.11 |
| 5,349,947 A | | 9/1994 | Newhouse et al. |
| 5,385,140 A | | 1/1995 | Smith |
| 5,427,089 A | * | 6/1995 | Kraemer ................. 128/200.23 |
| 5,584,285 A | * | 12/1996 | Salter et al. ............ 128/200.21 |
| 5,586,551 A | * | 12/1996 | Hilliard .................. 128/203.29 |
| 5,645,049 A | * | 7/1997 | Foley et al. ............ 128/203.29 |
| 5,813,401 A | * | 9/1998 | Radcliff et al. ......... 128/205.24 |
| 5,881,718 A | * | 3/1999 | Mortensen et al. .... 128/203.11 |
| 6,176,234 B1 | * | 1/2001 | Salter et al. ........... 128/200.14 |

FOREIGN PATENT DOCUMENTS

| | | |
|---|---|---|
| DE | 24 02 192 | 1/1974 |
| EP | 0 626 180 A1 | 11/1994 |

* cited by examiner

Primary Examiner—Weilun Lo
Assistant Examiner—Virendra Srivastava
(74) Attorney, Agent, or Firm—Merchant & Gould P.C.

(57) ABSTRACT

The invention describes a mouthpiece for an inhalation therapy unit wherein an aerosol for inhalation is prepared for a patient, said mouthpiece comprising a substantially tubular base (1), in the wall of which an orifice (2) is formed, and a flat, elastic valve member (3), which is adapted in dimension and shape to the orifice (2) for the closing thereof and which is secured to the mouthpiece in such a manner that during an inspiration process through the mouthpiece the orifice (2) is closed and during an expiration process directed into the mouthpiece the orifice (2) is opened. According to the invention, at least one enlarged contact surface (6, 8, 11, 13, 15, 16) is provided at the orifice (2) for the accumulation and holding of an amount of liquid by adhesion. This contact surface is established both by an outwardly directed collar (6, 8, 11) surrounding the orifice and by a narrow bar (13, 15, 16) which extends into the orifice (2) for example transversely through the center of the orifice in longitudinal direction of the mouthpiece or transversely across the mouthpiece.

8 Claims, 4 Drawing Sheets

MOUTH PIECE FOR INHALATION THERAPY UNITS

BACKGROUND OF THE INVENTION

The present invention relates to a mouthpiece for inhalation therapy units comprising the features of the preamble of patent claim 1.

Such a mouthpiece is known from the utility model G 93 21 308.5, which is fitted onto an outlet connecting member of the inhalation therapy unit for inhalation of a drug-containing aerosol produced in an inhalation therapy unit. The known mouthpiece comprises a check valve, which closes an orifice formed in the wall of the mouthpiece during the inhalation process, so that during the inhalation process the patient inhales the aerosol produced by the therapy unit. During exhalation, the valve member opens the orifice so that the respiratory air is removed directly from the mouthpiece and does not enter the therapy unit in a considerable amount. The known mouthpiece is constructed in such a manner that the orifice is provided in a substantially flat wall portion of the mouthpiece. The check valve is formed as a flat, elastic valve member, the dimensions and shape of which are adapted to the orifice for the closing thereof. The valve member is secured externally on the base in the region of the flat wall portion by means of a clamping device in such a manner that in its home position it abuts against the base on account of the effective elastic forces and closes the orifice. For the opening of the orifice the valve member can be raised partially from the base by means of the respiratory air flow.

In the known mouthpiece it has become evident that aerosol droplets accumulate in the region of the orifice or on the elastic valve element itself. This accumulation of liquid is so strong that the accumulated droplets spatter into the environment when the orifice is opened, i.e. when the valve member is raised during the expiration process. In this manner aerosol droplets can spatter into the face or eyes of the patient

SUMMARY OF THE INVENTION

It is therefore the object of the invention to improve the known mouthpiece for inhalation therapy units in such a manner that the spattering of liquid is avoided when the orifice formed in the base of the mouthpiece is opened by the valve member The object is solved by a mouthpiece for inhalation therapy units which an aerosol for inhalation is produced for a patient to inhale, said mouthpiece having a substantially tubular base in the wall of which an orifice is formed, and a flat, elastic valve member adapted in dimension and shape to the orifice for the closing thereof, and which is secured to the mouthpiece in such a manner that during an inhalation process through the mouthpiece the orifice is closed and during an exhalation process directed into the mouthpiece the orifice is opened, wherein at least one enlarged contact surface is provided at the orifice for the accumulation and holding of an amount of liquid by adhesion It is advantageous for the enlarged contact surface to be provided especially on the side of the orifice lying opposite the securement position of the valve member.

According to the invention, the enlarged contact surface can be created in that a collar is formed on the margin of the orifice, the edge of which forms an abutment surface for the valve member.

Furthermore, the enlarged contact surface can be created in that a bar extending into the opening of the mouthpiece is provided. Advantageously the bar extends in the longitudinal direction of the base. The bar also prevents the valve member from being suctioned into the mouthpiece.

In a further configuration, the bar extends under the plane of the orifice into the base. In this manner, the size of the surface, namely the side surface of the bar which is prepared as the enlarged contact surface, is increased.

In order to also partially include the inside wall of the mouthpiece as the enlarged contact surface according to the invention, it is advantageous to provide an extension bar that joins onto the bar arranged in the orifice and extends on the inside wall of the base.

Especially for the purpose of the return of the liquid, a cross-bar is provided that joins onto the bar or extension bar arranged in the orifice and extends transversely across the base.

In a further configuration, a securement aperture is provided in the base for securing the valve member in the proximity of the orifice, which can be for example a slot. As a counterpart, the flat, elastic valve member comprises a securement protrusion that can be inserted into the securement aperture to secure the valve member.

In an especially advantageous configuration, a wedge-shaped protrusion is provided on the outer wall of the base so that the valve member can be secured onto the mouthpiece essentially free of initial stress. In this respect it is advantageous for the securement aperture to be arranged in the wedge-shaped protrusion.

In summary, the invention describes a mouthpiece for an inhalation therapy unit in which an aerosol for inhalation is produced to inhale for a patient, said mouthpiece comprising a substantially tubular base, in the wall of which an orifice is formed, and a flat, elastic valve member which is adapted in dimension and shape to the orifice for the closing thereof, and which is secured to the mouthpiece in such a manner that during an inhalation process through the mouthpiece the orifice is closed and during an exhalation process directed into the mouthpiece the orifice is opened. According to the invention, at least one enlarged contact surface is provided at the orifice for the accumulation and holding of an amount of liquid by adhesion. This contact surface is established both by an outwardly directed collar surrounding the orifice and by a narrow bar that extends into the orifice in the longitudinal direction of the mouthpiece or transverse to the mouthpiece.

BRIEF DESCRIPTION OF THE DRAWINGS

The invention is described in more detail in the following on the basis of an embodiment and with reference to the enclosed drawings, which show.

DETAILED DESCRIPTION

Figure 1:
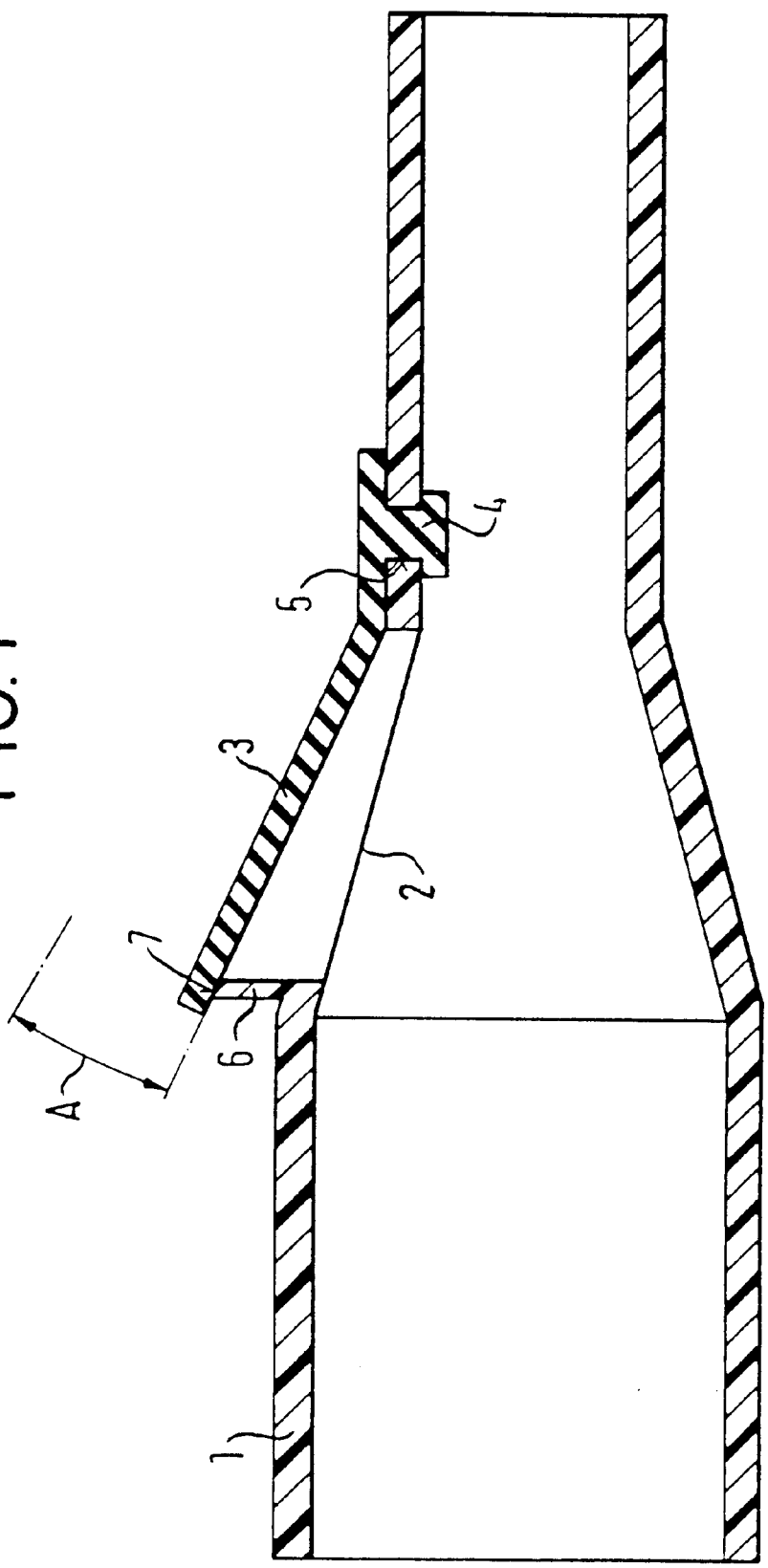
FIG. 1 a cross-sectional view of a first embodiment of the mouthpiece according to the invention.
Figure 2:
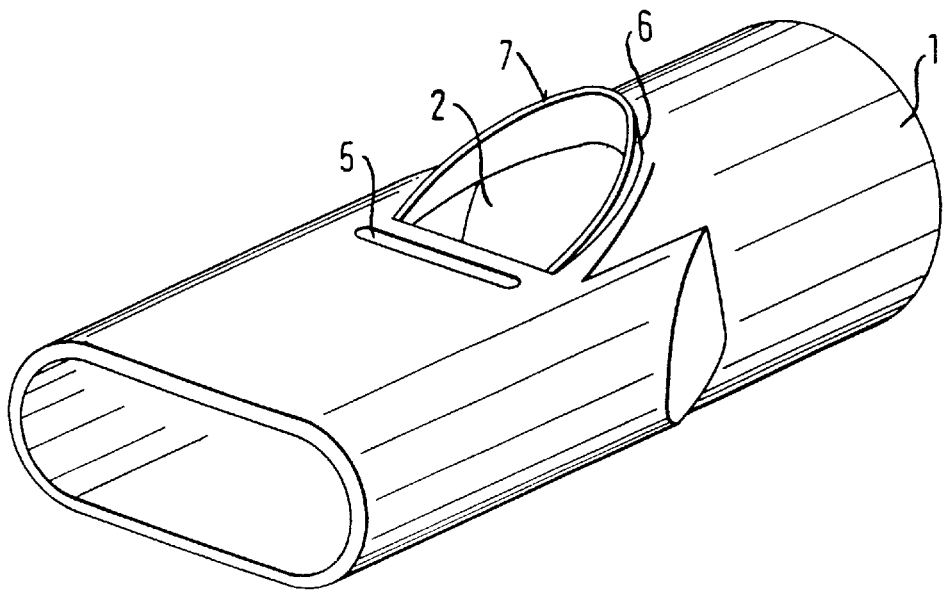
FIG. 2 a perspective view of the first embodiment of the mouthpiece of the invention according to FIG. 1 (without the valve member), FIG. 3 a perspective view of a second embodiment of the mouthpiece according to the invention (without the valve member), FIG. 4 a perspective view of a third embodiment of the mouthpiece according to the invention (without the valve member)

A first embodiment of the mouthpiece, according to the invention is represented in FIGS. 1 and 2. FIG. 1 shows a cross-sectional view in the longitudinal direction of the mouthpiece which results when the mouthpiece shown in FIG. 2 is bisected in the in longitudinal direction. As shown by FIGS. 1 and 2, the mouthpiece comprises a substantially tubular base 1, in the wall of which an orifice 2 is formed. As shown in FIG. 1, a flat, elastic valve member 3 is secured to the mouthpiece in that a securement protrusion 4 of the valve member 3 is inserted through a securement aperture 5 of the mouthpiece and secured. The valve member 3 is not shown in FIG. 2. However, as can be clearly seen from FIG. 1, the valve member 3 closes the orifice 2 when the patient inspires inhales through the mouthpiece since it is adapted in dimension and shape to the orifice 2. When the patient exhales into the mouthpiece the valve member 3 is raised so that the orifice 2 is opened. The valve member 3 moves in this connection approximately within the range A indicated in FIG. 1.

The enlarged contact surface according to the invention is constructed in the embodiment represented in FIGS. 1 and 2 by a collar 6 surrounding the orifice 2. The valve member 3 abuts against the upper edge 7 of the collar 6. Observed from the securement position of the valve member 3, the height of the collar 6 increases continually and reaches a maximum at the end lying opposite the securement position. The edge 7 of the collar 6 provides the valve member 3 with a flat abutment surface so that the valve member 3 can close the orifice 2 along the edge 7 of the collar 6. In the region of the securement position the valve member 3 abuts outwardly against the wall of the base 1. In this respect the securement aperture 5 is advantageously constructed as a slot that extends practically over the entire width of the orifice 2. In this manner a close abutment of the valve member 3 at the securement position is guaranteed along with a secure mounting of the valve member 3 on the mouthpiece When in the course of an inhalation therapy the patient inhales and exhale through the mouthpiece, aerosol droplets that were either not inhaled or were exhaled again by the patient, or which reached into the mouthpiece from the inhalation therapy unit during breathing intervals, precipitate on the collar 6, which forms the enlarged contact surface at the orifice 2 according to the invention. Due to the enlarged contact surface, an improved adhesion of larger amounts of liquid and a return of the accumulated liquid into the interior of the mouthpiece are achieved. Also, larger droplets are hardly detached and cast out entirely or partially by the valve member 3 moving during the breathing pattern, so that a spattering of the liquid accumulating on the enlarged contact surface 6 at the orifice 2 no longer occurs. On the contrary, the enlarged contact surface 6 at the orifice 2 has the effect that larger accumulations of liquid, which can form in the case of therapeutic applications of longer duration, can be returned in the form of droplets into the interior of the mouthpiece by gravity so that the accumulation of a critical amount of liquid susceptible to detachment by the moving valve member 3 could reoccur is safely avoided.

Figure 3:
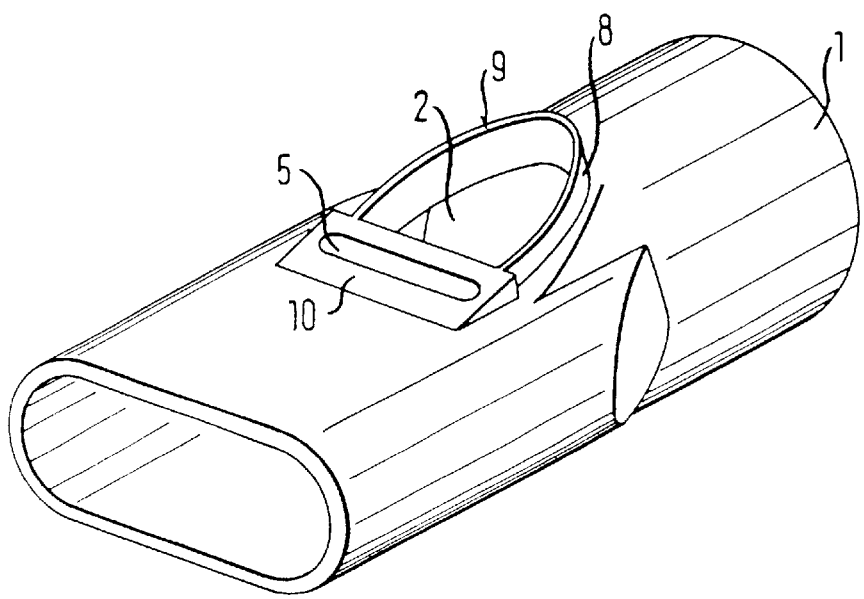

In FIG. 3 a further embodiment of the mouthpiece according to the invention with enlarged contact surface is represented. Apart from the differences explained in the following, the construction of the second embodiment conforms with that of the first embodiment which is referred to. In a manner similar to the first embodiment, also in the embodiment according to FIG. 3 a collar 8 is constructed at the margin of the orifice 2, on the edge 9 of which the valve member rests (not shown in FIG. 3). However, contrary to the first embodiment, the height of the collar 8 is almost constant. In the region of the securement position for the valve member a wedge-shaped protrusion 10 is provided on the wall of the mouthpiece. The surface of the wedge-shaped protrusion 10 facing the valve member is designed in such a manner that the edge 9 of the collar 8 is continued, i.e. the wall of the wedge-shaped protrusion 10 corresponding to the height of the collar 8 faces the orifice 2. As in the case of the first embodiment, at the securement position of the valve member a securement aperture 5 is provided, again in the form of a slot, through which a securement protrusion of the valve member can be inserted and secured. The valve member then abuts against the previously mentioned surface of the wedge-shaped protrusion 10 and on the edge 9 of the collar 8 and thus closes the orifice 2 during the inhalation processes.

The configuration of the second embodiment guarantees that the valve member is secured essentially free of initial stress on the mouthpiece. Thus the raising of the mouthpiece and the opening of the orifice takes place upon each exhalation directed into the mouthpiece, without the resistance of an initially stressed valve member needing to be overcome. The arrangement of the valve member free of initial stress on the mouthpiece effectively prevents a fluttering of the valve member by its own resonance and thus assists in avoiding the splattering of droplets.

Figure 4:
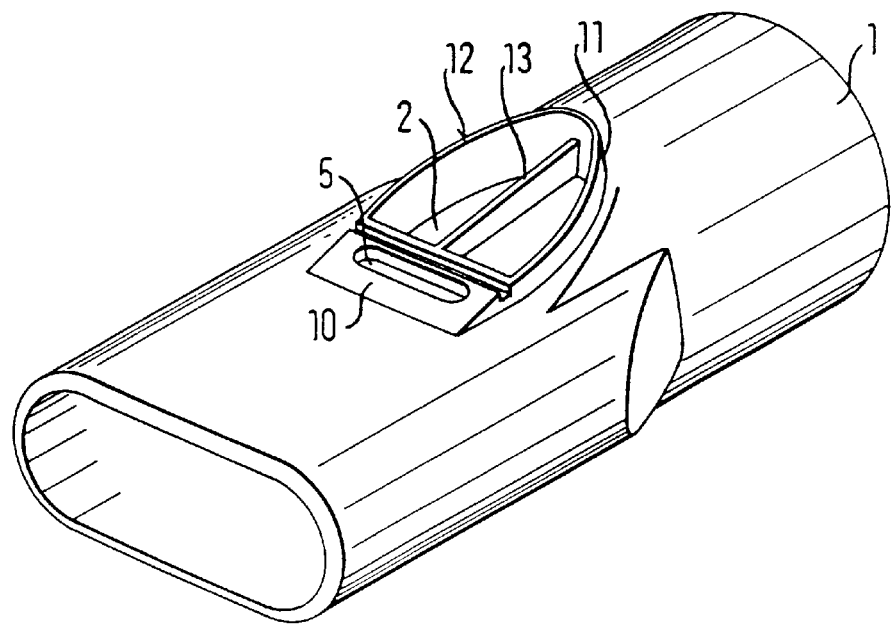

In FIG. 4 a third embodiment of the mouthpiece according to the invention is shown, wherein a collar 11 is constructed at the orifice 2 of the substantially tubular base 1 of the mouthpiece in such manner that an edge 12 of the collar 11 is continued with the aid of a wedge-shaped protrusion 10 in such a manner that a valve member secured in the region of the wedge-shaped protrusion 10 closes the orifice 2. As in the case of the first and second embodiment, for the securement of the valve member a slot 5 is provided in the wedge-shaped protrusion 10 of the wall of the mouthpiece, into which a securement protrusion of the valve member can be inserted and secured. Parallel to the slot 5, and thus parallel to the margin of the orifice 2, a groove is formed in the wedge-shaped protrusion 10, as shown by FIG. 4. In this manner, the edge 12 of the collar 11 is reproduced in the region of the wedge-shaped protrusion 10. The surface of the wedge-shaped protrusion 10 facing the valve member is arranged in a plane with the edge 12 of the collar 11. Accordingly, also in the case of this embodiment, the valve member abuts essentially free of any initial stress. In this embodiment, the collar 11 has almost constant height, since the plane of the edge 12 extends substantially parallel to the surface of the wall portion of the base 1 in which the orifice 2 is formed.

In the third embodiment of the invention, as shown in FIG. 4, a bar 13 is provided that extends in the longitudinal direction of the mouthpiece through the orifice 2. At the end of the bar 13 lying opposite the securement position of the valve member, the edge of the bar 13 facing the valve member lies below the edge 12 of the collar 11 formed at the orifice 2, so that a contact of the valve member with the bar 13 is avoided. By means of the bar 13 an enlarged contact surface according to the invention is created additionally that interacts with the enlarged contact surface of the collar 11 and produces additional adhesional forces away from the edge 12 towards the interior of the base. At the position of the contact surface of the collar 11 at which the bar 13 meets the collar 11, further larger accumulations of liquid can be held safely by the contact surfaces according to the invention so that the danger of the detachment of liquid droplets due to the movement of the valve member during exhalation by the patient is further reduced. Furthermore, it is achieved by means of the bar 13 that in the case of excessively strong inhalation the valve member is not inadvertently suctioned into the opening.

The bar 13 has a rectangular or trapezoidal cross-section. In the case of the trapezoidal cross-section, the narrow edge advantageously faces the valve member. In this manner the return of liquid accumulations is facilitated and the ejectability from the mold in the production of the mouthpiece by injection molding is supported.

Figure 5:
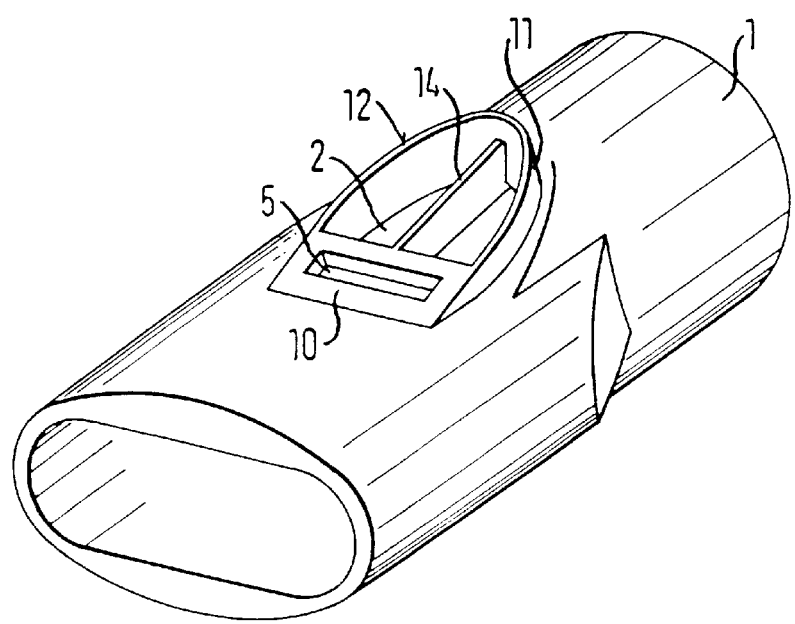
FIG. 5 a perspective view of a fourth embodiment of the mouthpiece according to the invention (without the valve member)

A fourth embodiment of the invention is explained in the following with reference to FIGS. 5 and 6; this embodiment also conforms in many respects with the embodiments already described so that a description of the mutual features is not repeated in all detail. Also in the case of the fourth embodiment, a bar 14 is provided that extends in the longitudinal direction of the mouthpiece through the orifice 2. The bar 14 extends moreover under the plane of the orifice 2 into the base 1 of the mouthpiece, as shown in FIG. 6.

At the end of the bar 14 lying opposite the securement position of the valve member, the edge of the bar 14 facing the valve member lies below the edge 12 of the collar 11 constructed at the orifice 2.

Figure 6:
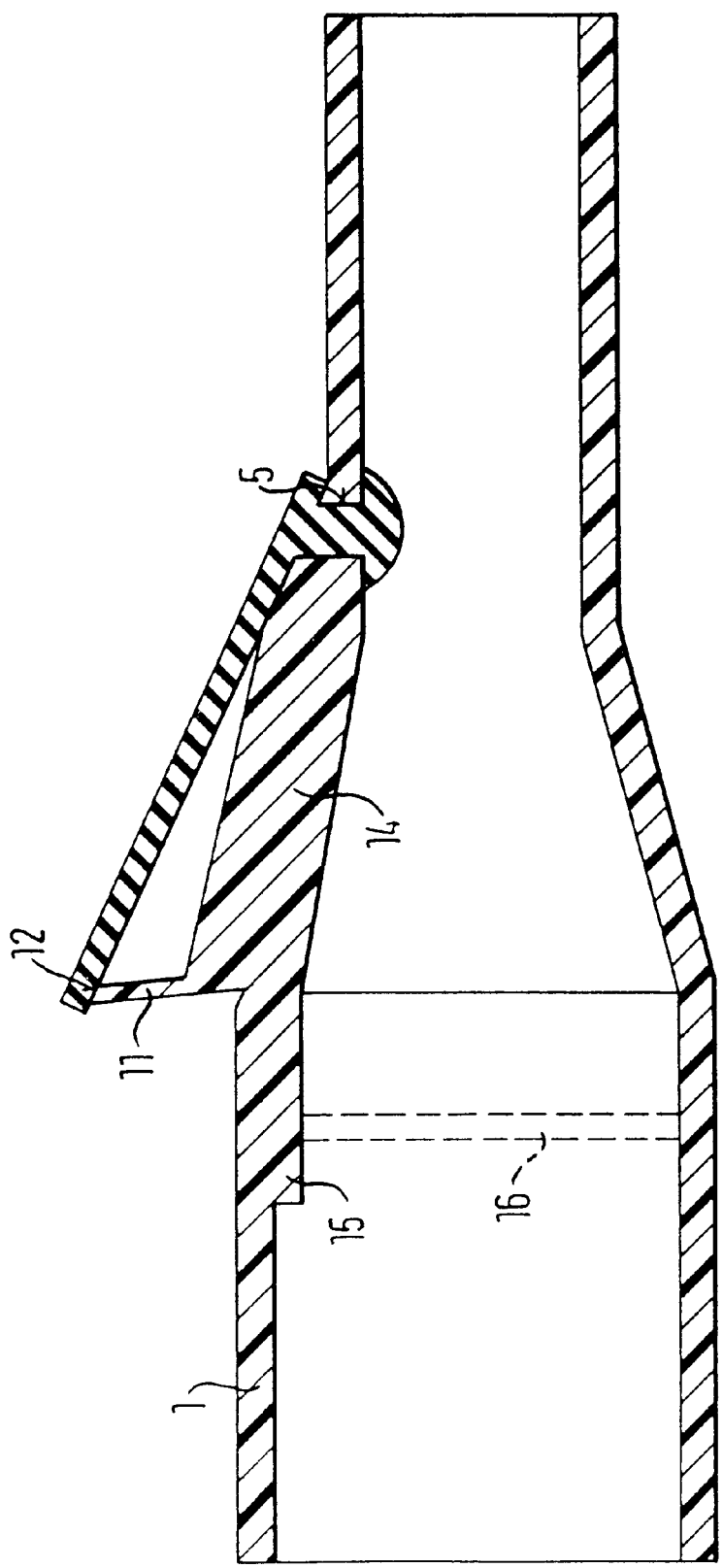
FIG. 6 a cross-sectional view of the fourth embodiment of the mouthpiece according to the invention.

In the fourth embodiment the bar 14 is continued into the interior of the mouthpiece in the form of an extension bar 15, such as shown in FIG. 6. On the one hand, in this manner the size of the enlarged contact surface located directly in the orifice 2 is increased, since the bar 14 extends a corresponding distance below the plane of the orifice 2. On the other hand, a part of the inside wall of the mouthpiece is incorporated into the enlarged contact surface according to the invention, since by means of the extension bar 15 on the inside wall of the base 1 of the mouthpiece the liquid accumulations in the orifice 2 are acted upon in such a manner that these also adhere to the inside wall of the mouthpiece or the extension bar 15, respectively, and thus tend to be drawn into the interior of the mouthpiece. In this manner the liquid is practically conducted out of the orifice 2, so that there is no longer any contact with the valve member and spattering is not possible.

A cross-bar 16 extending transversely across the base 1 of the mouthpiece can be provided on the bar 14 or its extension 15, which is only indicated however in FIG. 6 with a dotted line in the region of the extension 15. The cross-bar 16 assists the return of liquid accumulations which are led to the cross-bar 16 by means of the bar 14 and its extension 15.

What is claimed is:

1. A mouthpiece for inhalation therapy units in which an aerosol for inhalation by a patient is produced, comprising:

a substantially tubular base having a sidewall and an orifice defined in the sidewall;

a flat elastic valve member having a size and shape suitable for closing the orifice, having one portion secured to the base and a second portion that is free, whereby during inhalation through the mouthpiece the orifice is closed and during exhalation into the mouthpiece the orifice is opened by movement of the free end of the valve member away from the base; and a contact area for accumulating and holding by adhesion liquid from aerosol to be inhaled and thereby avoiding the accumulation of liquid from aerosol for inhalation on the valve member, wherein the contact area is provided opposite, with respect to the orifice, to a place where the valve member is secured to the base and the contact area comprises a collar extending outward from the base, the collar having an edge that forms an abutment surface for the valve member.

2. A mouthpiece according to claim 1, wherein the edge that forms an abutment surface is an upper edge of the collar.

3. A mouthpiece for inhalation therapy units in which an aerosol for inhalation by a patient is produced, comprising:

a substantially tubular base having a sidewall and an orifice defined in the sidewall;

a flat elastic valve member having a size and shape suitable for closing the orifice, having one portion secured to the base and a second portion that is free, whereby during inhalation through the mouthpiece the orifice is closed and during exhalation into the mouthpiece the orifice is opened by movement of the free end of the valve member away from the base;

a contact area for accumulating and holding by adhesion liquid from aerosol to be inhaled and thereby avoiding the accumulation of liquid from aerosol for inhalation on the valve member; and a bar extending across the orifice, wherein the bar has an upper edge that is below and spaced from the valve member when the valve member is in a resting position.

4. A mouthpiece according to claim 3, wherein the contact area is provided opposite, with respect to the orifice, to a place where the valve member is secured to the base.

5. A mouthpiece according to claim 4, wherein the contact area comprises a collar extending outward from the base, the collar having an edge that forms an abutment surface for the valve member.

6. A mouthpiece according to claim 3, wherein in the bar extends in a longitudinal direction of the base.

7. A mouthpiece according to claim 3, wherein the bar extends into the interior of the base beyond an inner surface of the sidewall of the base.

8. A mouthpiece according to claim 7, wherein the bar extends outside the edges of the orifice.

* * * * *